United States Patent [19]

Shono

[11] Patent Number: 4,544,766
[45] Date of Patent: Oct. 1, 1985

[54] PROCESS FOR PREPARING ARYL ACETIC ACID DERIVATIVES

[75] Inventor: Tatsuya Shono, Kyoto, Japan

[73] Assignee: Otsuka Kagaku Yakuhin Kabushiki Kaisha, Japan

[21] Appl. No.: 352,546

[22] Filed: Feb. 26, 1982

[30] Foreign Application Priority Data

Mar. 6, 1981 [JP] Japan .................................. 56-33007
Sep. 21, 1981 [JP] Japan ............................... 56-150132
Feb. 22, 1982 [JP] Japan ................................. 57-27962

[51] Int. Cl.$^4$ ............................................. C07C 69/76
[52] U.S. Cl. ...................... 560/75; 549/446; 549/496; 560/8; 560/105; 562/405; 562/478; 562/489; 562/490; 562/496
[58] Field of Search .................... 562/496, 478; 560/75

[56] References Cited

U.S. PATENT DOCUMENTS 3,957,891 5/1976 Gelfand ............................... 562/496

FOREIGN PATENT DOCUMENTS 56-152445 11/1981 Japan .

OTHER PUBLICATIONS

Synthetic Communications, 6 (5), pp. 349–355 (1976).

Primary Examiner—Ethel G. Love
Attorney, Agent, or Firm—Larson and Taylor

[57] ABSTRACT

This invention relates to a process for preparing an aryl acetic acid derivative represented by the formula

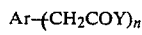

Ar$-$(CH$_2$COY)$_n$ comprising hydrolyzing in an alkaline substance a dichloroethenyl compound represented by the formula

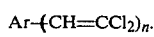

Ar$-$(CH=CCl$_2$)$_n$.

3 Claims, No Drawings

PROCESS FOR PREPARING ARYL ACETIC ACID DERIVATIVES

This invention relates to novel processes for preparing aryl acetic acid derivatives and particularly to novel processes for preparing aryl acetic acid derivatives having the formula $$Ar\text{---}(CH_2COY)_n \qquad (I)$$

wherein Ar is phenyl, polynuclear aromatic group or heterocyclic group optionally substituted with halogen, hydroxyl, alkyl, alkenyl, aralkyl, alkoxy, acyloxy, aralkyloxy or phenoxy having or not having substituents, the substituent of said Ar is 1 to 3 in number and may be different or the same, n is an integer of 1 to 3, and Y is hydroxyl, amino or alkoxy.

The foregoing aryl acetic acid derivatives having the formula (I) are useful as intermediates for preparing pharmaceutical compositions. For Example, the aryl acetic acid derivatives having the formula (I) (hereinafter referred to as "AD") include p-hydroxyphenyl acetic acid and p-hydroxyphenyl acetic acid amide which are significant materials for preparing antibiotic substances and β-blocking agents, respectively.

Several processes for preparing AD have been heretofore developed. But in the conventional processes, AD are not produced by hydrolysis of a dichloroethenyl compound represented by the formula $$Ar\text{---}(CH=CCl_2)_n \qquad (II)$$

wherein Ar and n are as defined above.

Heretofore attempts have been made indeed to prepare AD by hydrolysis of the dichloroethenyl compound having the formula (II) but in vain, as apparent from the statement in Synthetic Communications, 6 (5), pages 349–355 (1976) that it is impossible to produce phenyl acetic acid derivatives by hydrolysis of dichloroethenyl compounds. The foregoing publication discloses a process in which a dichloroethenyl compound is reacted with diborane to form a boron compound which is then oxidized with chromic acid, whereby a phenyl acetic acid derivative is prepared. However, the process proposed therein suffers various drawbacks of requiring a number of steps, using expensive reagents and the oxidizing agent presently posing pollution problems, etc.

Processes are known for preparing dichloroethenyl compounds having the formula (II). For example, the following processes are known: those involving a treatment of tribromopropenyl compound with potassium butoxide, sodium butoxide or like special alkali (see Japanese Unexamined Patent Publication No. 125252/1976), those entailing a treatment of tetrachloro compound with a strong base (see Bull. Chem. Soc., Japan, 52 (5), pages 1511–1514 (1979)), etc. These known methods, however, do not use a trichloromethyl carbinol serving as the starting material and have the deficiencies of requiring metal alkoxide or like expensive reagents, giving end products in low yields, involving numerous steps for preparing the end product, etc. To our knowledge, there is no literature other than Angew. Chem. Int. Ed. Engl., 16, pages 57–58 (1977) which discloses the preparation of dichloroethenyl compounds by electrolytic reduction of trichloromethyl carbinol. However, the process described in this publication essentially requires, as an electrode, mercury which has been recently drawing attention because of pollution and toxicity problems and tends to get out of use. The disclosed process also involves an electrolytic reduction at a constant potential voltage, and thus have serious disadvantages of being very low in current efficiency and hence uneconomical and being very poor in yield, that is, usually as low as 20 to 30%, about 80% at the highest, etc.

The main object of this invention is to provide a process for preparing AD by hydrolyzing a dichloroethenyl compound having the formula (II).

Another object of this invention is to provide a process for preparing AD from a dichloroethenyl compound of the formula (II) by a single step.

Still another object of this invention is to provide a process for preparing AD without using an expensive reagent.

A further object of the invention is to provide a process for preparing AD without using an oxidizing agent which is now problematic in respect of its pollution.

Still a further object of the invention is to provide a process for preparing a dichloroethenyl compound of the formula (II) in a high yield by a simplified procedure without using a special reagent.

The other characteristics of the invention are apparent from the following description.

According to this invention, AD can be prepared in high yields by hydrolysis of the dichloroethenyl compound represented by the formula $$Ar\text{---}CH=CCl_2)_n \qquad (II)$$

in the presence of an alkaline substance.

The group Ar in the formulae (I) and (II) represents phenyl, polynuclear aromatic group or heterocyclic group all optionally substituted.

Preferred examples of useful polynuclear aromatic groups are α-naphthyl, β-naphthyl, anthranyl, pyrenyl and the like. Those of useful heterocyclic groups are cyclic groups containing oxygen, nitrogen, sulphur and like atoms. Exemplary of the same are furyl, tetrahydrofuryl, pyranyl, tetrahydropyranyl, pyrrolyl, pyridinyl, thienyl, oxazolyl, morpholinyl, thiazynyl, etc.

Examples of useful substituents of phenyl, polynuclear aromatic group or heterocyclic group are halogen, hydroxyl, alkyl, alkenyl, aralkyl, alkoxy, acyloxy, aralkyloxy, phenoxy, or phenoxy having substituents. The substituent of said Ar is 1 to 3 in number and may be different or the same. The number n is an integer of 1 to 3. Useful halogen atoms are fluorine, chlorine, bromine, iodine, etc. Preferred examples of useful alkyl groups are methyl, ethyl, butyl, octyl, decyl and the like having 1 to 10 carbon atoms. Preferred examples of useful alkenyl groups are vinyl, allyl, propenyl, hexenyl, decenyl and the like having 2 to 10 carbon atoms. Those of useful aralkyl groups are benzyl, phenylethyl, phenylbutyl and the like having 7 to 10 carbon atoms. Those of useful alkoxy groups are methoxy, ethoxy, hexyloxy, methylenedioxy and the like having 1 to 6 carbon atoms. Those of useful acyloxy groups are acetoxy, butyryloxy, valeryloxy and the like having 2 to 6 carbon atoms. Those of useful aralkyloxy groups are benzyloxy, phenetyloxy and the like having 7 to 10 carbon atoms. Those of useful substituents of the phenoxy group are halogen, nitro, alkyl, hydroxy, alkoxy, aryl and the like.

Y in the foregoing formula (I) represents hydroxyl, amino or alkoxy. Preferred examples of alkoxy groups are methoxy, ethoxy, propoxy, butoxy, pentyloxy, hexyloxy and the like having 1 to 6 carbon atoms.

As mentioned in Synthetic Communications 6 (5), pages 349–355 (1976), it has been thought impossible to produce phenyl acetic acid derivatives by hydrolysis of dichloroethenyl compounds. In this situation, we conducted extensive research and found it possible to hydrolyze a dichloroethenyl compound of the formula (II) in the presence of an alkaline substance. More specifically stated, a dichloroethenyl compound is heated in water, an organic solvent or a solvent mixture thereof containing an alkaline substance to obtain AD. With the present invention, it is essential that the dichloroethenyl compound of the formula (II) be hydrolyzed in the presence of an alkaline substance. Hydrolysis of the compound (II) in the presence of an acid is unable to form AD as contemplated. Usable as the organic solvent are, for example, methanol, ethanol or like alcohols, dimethylformamide, dioxane, tetrahydrofuran and like ethers, benzene, xylene and like aromatic hydrocarbons, etc. which are stable in admixture with an alkaline substance. The alkaline substance to be used in the present invention is suitably selected from known compounds, depending on a specific type of the end product contemplated. For example, the aryl acetic acid derivative of the formula (I) in which Y is hydroxyl can be produced by hydrolyzing the dichloroethenyl compound (II) with use of a basic substance in the alkaline substance, such as sodium hydroxide, potassium hydroxide and like hydroxides of alkali metals, calcium hydroxide, barium hydroxide and like hydroxides of alkaline earth metals, sodium methylate, potassium butoxide and like metal alkoxides, and 1,8-diazabicyclo[5,4,0]undecene-7(DBU), etc. When using ammonia water, liquid ammonia, sodium amide, potassium amide or like amides of alkali metals in hydrolysis of the dichloroethenyl compound, the aryl acetic acid derivative of the present invention in which Y is amino can be obtained. Further AD in which Y is alkoxy can be produced by carrying out the hydrolysis using alcohol as the organic solvent, and one of the foregoing metal alkoxides as the alkaline substance, followed by the neutralization of the reaction mixture at the acidic side.

The amount of the alkaline substance to be used in the present process, although widely variable, is usually in the range of about 0.01 to about 10 mole, preferably about 0.1 to 5 mole, per mole of the compound (II). The heating temperature is not particularly limited but can be selected from a wide range. It is usually about 50° to about 200° C., preferably about 70° C. to 150° C.

According to the process of the present invention, AD as contemplated can be prepared from the dichloroethenyl compound of the formula (II) by a single procedure which is performed in a simple manner without using an expensive reagent or harmful oxidizing agent. It should be noted that the dichloroethenyl compound of the formula (II) in which Ar is phenyl substituted with hydroxyl is a novel compound.

With the present invention, any of the dichloroethenyl compounds (II) prepared by conventional methods is usable as the starting material. Such compounds can be readily produced for example by electrolytic reduction of trichloromethyl carbinol derivative expressed by the formula

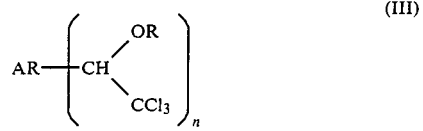

wherein R is hydrogen or acyl, and Ar and n are as defined above.

Examples of useful acyl groups represented by R are acetyl, propionyl, butyryl, etc.

The electrolytic reduction of the present invention is carried out in an organic solvent or a mixture of water and an organic solvent in the presence of an acid by using a diaphragm. Examples of useful organic solvents are those which are able to dissolve water to some extent and are inert in the course of electrolysis, such as methanol, ethanol and like alcohols, dioxane, methyl cellosolve and like ethers, acetonitrile, dimethylformamide, dimethylsulfoxide, etc. Usable as the required acid are, for example, all types of inorganic and organic acids, but usually it is preferred to employ hydrochloric acid, sulfuric acid and like mineral acids, benzenesulfonic acid, toluenesulfonic acid and like organic acids.

Examples of support electrolytes useful in this invention include those usually used such as tetraethyl ammonium chloride, tetramethyl ammonium chloride and the like hydrochlorides of tertiary amines, tetraethyl ammonium sulfate, tetramethyl ammonium sulfate and like sulfates of tertiary amines, tetraethyl ammonium salt of p-toluenesulfonic acid, tetramethyl ammonium salt of p-toluenesulfonic acid, tetramethyl ammonium salt of perchloric acid and like quaternary ammonium salts, sodium borofluoride, tetramethyl ammonium salt of borofluoric acid and like salts of borofluoric acid, alkali metal salt and alkaline earth metal salt of benzenesulfonic acid, toluenesulfonic acid and like arylsulfonic acids, etc. The amount of the support electrolyte to be used, although widely variable, is usually in the range of about 0.01 to 10 mole, preferably 0.1 to 5 mole, per mole of the trichloromethyl carbinol derivative (III). Useful electrodes are carbon, platinum, titanium, iron, stainless steel, nickel, lead, alloys predominantly comprising these compounds, and the like usually used in the art. From an economical point of view, it is preferred to use for example lead as a cathode and carbon as an anode. The electrolyte reduction of this invention is conducted at a constant current. Usable as the diaphragm is a membrane of a high molecular weight compound, ion-exchange membrane, glass filter, porous sheet and the like. The reaction temperature is not particularly limited, but is usually −10° to 100° C. The reaction smoothly proceeds in the vicinity of or at room temperature.

The electrolytic reduction of this invention eliminates the use of any special reagent and is feasible by a simplified procedure. Further, the foregoing reduction is able to give a dichloroethenyl compound of the formula (II) in high yield.

As stated above, a trichloromethyl carbinol derivative of the formula (III) is used as the starting material for the preparation of a dichloroethenyl compound of the formula (II) according to this invention. The derivative of the formula (III) wherein R is hydrogen, namely a compound of the formula

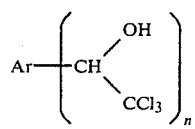

(III-a)

wherein Ar and n are as defined above is a known compound readily available. The derivative of the formula (III) wherein R is acyl, namely a compound of the formula

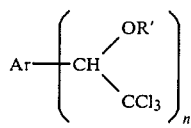

(III-b)

wherein R' is acyl, and Ar and n are as defined above is a novel compound undisclosed in any literature. The compound of the formula (III-b) is easily prepared for example by acylation of the compound of the formula (III-a). The acylation is carried out for example by reacting an acylation agent with the compound of the formula (III-a) in a suitable solvent in the presence of an organic base. In this case, the organic base is also usable as the solvent. Examples of solvents useful in this acylation are ethyl ether, tetrahydrofuran and like ethers, acetonitrile, benzene, toluene and like aromatic hydrocarbons, etc. Examples of useful bases are pyridine, picoline and the like, triethylamine, dimethylamine and like alkyl amines, etc. Examples of useful acylation agents are acetic acid anhydride, butyric acid anhydride and like acid anhydrides, acetyl chloride, propionyl chloride and like acid halides, etc. The acylation agent is used in usually 1 to 5 times, preferably 1.2 to 2 times, the stoichiometric amount of the compound of the formula (III-a). The acylation is conducted usually at $-30°$ to $150°$ C., preferably at $-10°$ to $100°$ C.

When the compound of the formula (III-b) is used as the starting material, the compound can be easily separated from the reaction mixture because of a high crystallinity of the compound, whereby a dichloroethenyl compound of the formula (II) having a higher purity is advantageously obtained in a higher yield.

The intermediate and end product of the present invention can be easily separated and purified by usual means such as extraction, concentration, distillation, recrystallization, column chromatography, and the like.

For a better understanding of the present invention, given below are reference examples and examples.

REFERENCE EXAMPLE 1

A 10 g quantity of tetraethyl ammonium salt of p-toluenesulfonic acid was dissolved in 60 ml of dimethylformamide containing 0.1 mole of chloroform. The solution was placed in a cathode chamber and in an anode chamber. Further 13.6 g (0.1 mole) of p-methoxybenzaldehyde and 0.01 mole of carbon tetrachloride was introduced into the cathode chamber. A glass filter was used as a diaphragm. Electrolysis was conducted at a constant current of 0.1 A. After current (2 F/mole) was passed, the reaction liquid was withdrawn from the cathode chamber. The carbon tetrachloride and chloroform were distilled off and the residue was extracted with methylene chloride. The methylene chloride was distilled off from the extract and the residue was distilled in a vacuum, giving trichloromethyl-4-methoxyphenyl carbinol. Yield 94.5%, b.p. 122°–124° C./1 mmHg.

REFERENCE EXAMPLE 2

A 0.1 mole quantity of p-hydroxyphenyl trichloromethyl carbinol was dissolved in 0.3 mole of pyridine. To the solution was dropwise added 0.22 mole of acetic acid anhydride with stirring. The resulting mixture was agitated for 2 hours. After completion of the reaction, the pyridine was distilled off at reduced pressure and the residue was washed with 50 ml of water. The crystals were filtered off to obtain ester of p-acetoxyphenyl trichloromethyl carbinol and acetic acid. Yield 98.5%, m.p. 152.5°–153° C.

REFERENCE EXAMPLE 3

The same procedure as in Reference Example 2 was repeated with the exception of using 0.1 mole of p-methoxyphenyl trichloromethyl carbinol to obtain ester of p-methoxyphenyl trichloromethyl carbinol and acetic acid. Yield 99.0%, m.p. 82°–82.5° C.

EXAMPLE 1

A 10 ml quantity of concentrated hydrochloric acid, 2.5 g of tetraethyl ammonium salt of p-toluenesulfonic acid and 5.5 g of triethyl ammonium chloride were dissolved in 60 ml of ethanol. The solution was placed in an anode chamber and a cathode chamber separated from each other by a diaphragm. In the cathode chamber was further introduced 10 m mole of p-benzyloxyphenyl trichloromethyl carbinol

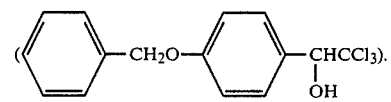

Then constant-current electrolysis was performed with use of lead as a cathode and carbon as an anode. After current (5 F/mole) was passed, the reaction liquid from the cathode chamber was added to 200 ml of water. The mixture was extracted four times with 50 ml of hexane. Then the extract was dried over anhydrous magnesium sulfate. The solvent was distilled off and the residue was purified by silica gel column chromatography, giving 2.54 of p-benzyloxyphenyl-dichloroethylene

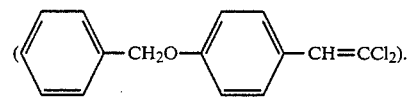

Yield 91.0%, m.p. 74.5°–76.5° C.

EXAMPLE 2

A 10 ml quantity of concentrated hydrochloric acid, 2.5 g of tetraethyl ammonium salt of p-toluenesulfonic acid and 5.5 g of triethyl ammonium chloride were dissolved in 60 ml of ethanol. The solution was placed in an anode chamber and a cathode chamber separated from each other by a diaphragm. In the cathode chamber was further introduced 10 m mole of p-hydroxyphenyl trichloromethyl carbinol

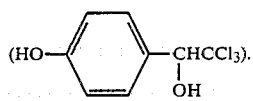

Then constant-current electrolysis was performed with use of lead as a cathode and carbon as an anode. After current (5 F/mole) was passed, the reaction liquid from the cathode chamber was added to 200 ml of water. The mixture was extracted four times with 50 ml of hexane. Then the extract was dried over anhydrous magnesium sulfate. The solvent was distilled off and the residue was purified by silica gel column chromatography, giving 1.80 g of p-hydroxy-β,β-dichlorostyrene

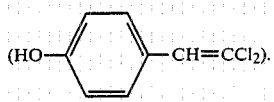

Yield 95.2%, m.p. 90°–91° C. IR (cm$^{-1}$) 3370, 1604, 1500, 1442, 1375, 1235, 1180, 1109, 909, 873, 821, 682.

EXAMPLE 3

A 50 ml quantity of methanol containing 3% of sulfuric acid was placed in an anode chamber and a cathode chamber separated from each other by a diaphragm. Further in the cathode chamber was introduced 2.415 g of p-hydroxyphenyl trichloromethyl carbinol. Constant-current electrolysis was effected with use of lead as both an anode and cathode. The reaction temperature was maintained at 45°–50° C. and current (3 F/mole) was passed. Then the same subsequent treatments as in Example 1 were conducted to obtain 1.83 g of p-hydroxy-β,β-dichlorostyrene.

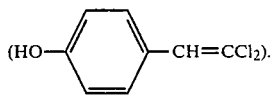

Yield 96.8%, m.p. 90°–91° C.

EXAMPLE 4

A 50 ml quantity of methanol containing 3% of sulfuric acid and 20% of water was placed in an anode chamber and a cathode chamber separated from each other by a diaphragm. Further in the cathode chamber was introduced 2.415 g of p-hydroxyphenyl trichloromethyl carbinol

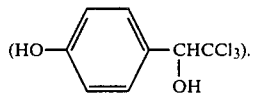

Constant-current electrolysis was effected with use of lead as both an anode and cathode. The reaction temperature was maintained at 45°–50° C. and current (3 F/mole) was passed. Then the same subsequent treatments as in Example 1 were conducted to obtain 1.79 g of p-hydroxy-β,β-dichlorostyrene

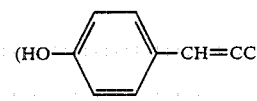

Yield 94.7%, m.p. 90°–91° C.

EXAMPLE 5

A 50 ml quantity of acetonitrile containing 3% of sulfuric acid was placed in an anode chamber and a cathode chamber separated from each other by an ion-exchange membrane. Further in the cathode chamber was introduced 2.415 g of p-hydroxyphenyl trichloromethyl carbinol. Constant-current electrolysis was effected with use of lead as both an anode and cathode. The reaction temperature was maintained at 50°–55° C. and current (3 F/mole) was passed. Then the same subsequent treatments as in Example 1 were conducted to obtain 1.84 g of p-hydroxy-β,β-dichlorostyrene

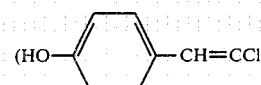

Yield 97.4%, m.p. 90°–91° C.

EXAMPLE 6

In an autoclave were placed 0.5 g of p-hydroxy-β,β-dichlorostyrene

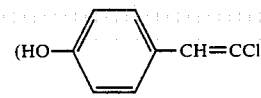

1.0 g of sodium hydroxide and 5 ml of methanol. The mixture was heated at 120°–130° C. for 4 hours. Then the methanol was distilled off. To the residue was added 10 ml of water and the mixture was refluxed for 30 minutes. After completion of the reaction, the reaction mixture was acidified by concentrated hydrochloric acid and was extracted three times with 10 ml of ether. The extract was dried over anhydrous magnesium sulfate and the ether was distilled off. The residue was purified by silica gel column chromatography by using benzene, n-hexane and ethyl acetate (10:10:3) as a developer solvent to afford 0.3 g of p-hydroxyphenylacetic acid

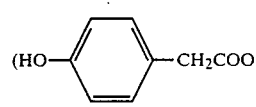

Yield 94.5%, m.p. 151°–152° C. NMR (CDCl$_3$, δ, ppm) 3.50 (s, 2H), 4.25 (b.s., 2H), 6.92 (m, 4H)

EXAMPLE 7

A 1 g quantity of p-benzyloxyphenyl dichloroethylene

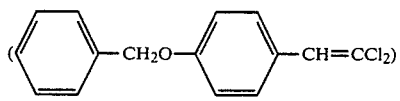

was dissolved in 10 ml of 95% ethanol containing 5 g of potassium hydroxide. The solution was refluxed for 4 hours. After completion of the reaction, the ethanol was distilled off and 50 ml of water was added to the residue. The mixture was extracted three times with 25 ml of ether. The aqueous phase was further acidified by hydrochloric acid and was extracted four times with 25 ml of ether. Two ether phases were combined and dried over anhydrous magnesium sulfate and then the ether was distilled off. The residue was recrystallized from chloroform, giving 80.2 mg of p-benzyloxy phenyl acetic acid

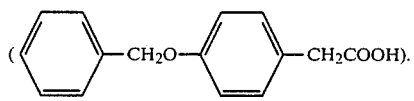

Yield 92.5%, m.p. 116°–118° C.

EXAMPLE 8

In an autoclave were placed 1.73 g of phenyldichloroethylene

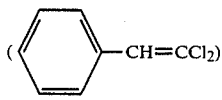

and 20 ml of concentrated aqueous ammonia solution. The mixture was heated at 100° C. for 4 hours. After completion of the reaction, the reaction mixture was cooled and the excess ammonia was removed at reduced pressure. The residue was filtered and the filtrate was distilled at reduced pressure to afford 1.272 g of phenylacetamide

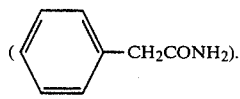

Yield 94.2%, m.p. 153°–155° C.

EXAMPLE 9

In an autoclave were placed 0.5 g of p-hydroxy-β,β-dichlorostyrene

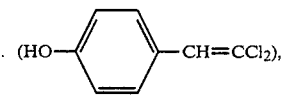

1.0 g of sodium hydroxide and 5 ml of methanol. The mixture was heated at 120°–130° C. for 4 hours. The methanol was distilled off. Thereafter the mixture was added to 9.7 ml of 10% sulfuric acid in small amounts for neutralization. The resulting mixture was extracted three times with 10 ml of ether. The extract was dried over anhydrous magnesium sulfate and the ether was distilled off. The residue was purified by silica gel column chromatography using a solvent mixture of benzene, n-hexane and ethyl acetate (10:10:3) to obtain 0.36 g of methyl ester of p-hydroxyphenyl acetic acid

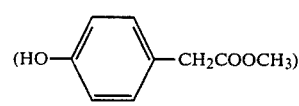

and 52 mg of p-hydroxyphenyl acetic acid

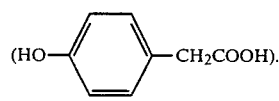

EXAMPLE 10

A 50 ml quantity of methanol containing 3% of sulfuric acid was placed in an anode chamber and a cathode chamber separated from each other by a diaphragm. Further in the cathode chamber was introduced 10 m mole of p-acetoxyphenyl trichloromethyl methylacetate

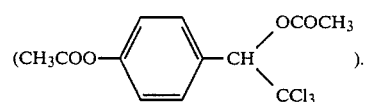

Constant-current electrolysis was effected with use of lead as both an anode and cathode. The reaction temperature was maintained at 45°–50° C. and current (3 F/mole) was passed. Then the same subsequent treatments as in Example 3 were conducted to obtain 1.8 g of p-hydroxy-β,β-dichlorostyrene

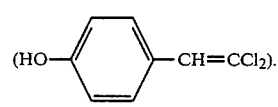

EXAMPLES 11–23

The same procedures as in Example 1 were repeated by using the starting materials shown in Table 1 given below. Table 1 also indicates the resulting products.

TABLE 1

| Example | Starting material | Reaction product | Yield (%) | Physical property |
|---|---|---|---|---|
| 11 | C₆H₅CH(OH)(CCl₃) | C₆H₅CH=CCl₂ | 96.2 | b.p. 95–96° C. (15 mmHg) |
| 12 | 4-CH₃O-C₆H₄-CH(OH)(CCl₃) | 4-CH₃O-C₆H₄-CH=CCl₂ | 91.5 | b.p. 127–129° C. (16 mmHg) |
| 13 | 3,4-(methylenedioxy)-C₆H₃-CH(OH)(CCl₃) | 3,4-(methylenedioxy)-C₆H₃-CH=CCl₂ | 90.8 | b.p. 95–96° C. (1 mmHg) |
| 14 | 2-furyl-CH(OH)(CCl₃) | 2-furyl-CH=CCl₂ | 89.0 | |
| 15 | 4-Cl-C₆H₄-CH(OH)(CCl₃) | 4-Cl-C₆H₄-CH=CCl₂ | 96.8 | b.p. 80–82° C. (2 mmHg) |
| 16 | 4-Cl-C₆H₄-CH(OCOCH₃)(CCl₃) | 4-Cl-C₆H₄-CH=CCl₂ | 94.0 | |
| 17 | 1-naphthyl-CH(OH)(CCl₃) | 1-naphthyl-CH=CCl₂ | 93.5 | m.p. 46–47.5° C. |
| 18 | 2-CH₃O-C₆H₄-CH(OH)(CCl₃) | 2-CH₃O-C₆H₄-CH=CCl₂ | 93.5 | b.p. 85–86° C. (2 mmHg) |
| 19 | 3-CH₃O-C₆H₄-CH(OH)(CCl₃) | 3-CH₃O-C₆H₄-CH=CCl₂ | 94.0 | b.p. 95–96° C. (5 mmHg) |
| 20 | 3-CH₃O-C₆H₄-CH(OCOCH₃)(CCl₃) | 3-CH₃O-C₆H₄-CH=CCl₂ | 94.2 | |
| 21 | Cl₃C-CH(OH)-C₆H₄-CH(OH)-CCl₃ | Cl₂C=CH-C₆H₄-CH=CCl₂ | 65.0 | m.p. 75–77° C. |

TABLE 1-continued

| Example | Starting material | Reaction product | Yield (%) | Physical property |
|---|---|---|---|---|
| 22 | CH₃O–C₆H₄–CH(OCOCH₃)(CCl₃) | CH₃O–C₆H₄–CH=CCl₂ | 93.0 | b.p. 127–129° C. (16 mmHg) |
| 23 | CH₃–C₆H₄–CH(OCOCH₃)(CCl₃) | CH₃–C₆H₄–CH=CCl₂ | 95.3 | b.p. 38–40° C. |

EXAMPLES 24–38

The same procedures as in Example 6 or 9 were repeated by using the staring materials shown in Table 2 given below. Table 2 also indicates the resulting products.

TABLE 2

| Example | Starting material | Reaction product | Yield (%) | Physical property |
|---|---|---|---|---|
| 24 | C₆H₅–CH=CCl₂ | C₆H₅–CH₂COOH | 91.8 | m.p. 74–76° C. |
| 25 | C₆H₅–CH=CCl₂ | C₆H₅–CH₂COOCH₃ | 84.0 | b.p. 215° C. |
| 26 | C₆H₅–CH=CCl₂ | C₆H₅–CH₂COOC₂H₅ | 82.5 | b.p. 121° C. (20 mmHg) |
| 27 | CH₃O–C₆H₄–CH=CCl₂ | CH₃O–C₆H₄–CH₂COOH | 89.8 | m.p. 79–81° C. |
| 28 | 3,4-methylenedioxyphenyl–CH=CCl₂ | 3,4-methylenedioxyphenyl–CH₂COOH | 90.0 | m.p. 121–123° C. |
| 29 | 2-furyl–CH=CCl₂ | 2-furyl–CH₂COOH | 84.5 | m.p. 62–63.5° C. |
| 30 | Cl–C₆H₄–CH=CCl₂ | Cl–C₆H₄–CH₂COOH | 89.5 | m.p. 101–102.5° C. |
| 31 | 1-naphthyl–CH=CCl₂ | 1-naphthyl–CH₂COOH | 90.4 | m.p. 129–130° C. |
| 32 | 2-OCH₃–C₆H₄–CH=CCl₂ | 2-OCH₃–C₆H₄–CH₂COOH | 92.7 | m.p. 121–123° C. |

TABLE 2-continued

| Example | Starting material | Reaction product | Yield (%) | Physical property |
|---|---|---|---|---|
| 33 | CH₃O-C₆H₄-CH=CCl₂ | CH₃O-C₆H₄-CH₂COOH | 89.0 | m.p. 68–70° C. |
| 34 | Cl₂C=CH-C₆H₄-CH=CCl₂ | HOOCCH₂-C₆H₄-CH₂COOH | 87.2 | m.p. 248–251° C. |
| 35 | (CH₃O)₂C₆H₃-CH=CCl₂ | (CH₃O)₂C₆H₃-CH₂COOH | 93.8 | m.p. 80–81.5° C. |
| 36 | Cl,HO-C₆H₃-CH=CCl₂ | Cl,HO-C₆H₃-CH₂COOH | 91.3 | NMR δ 3.62 (2H, s) 6.90–7.53 (3H, m) 8.88 (2H, s) |
| 37 | CH₃-C₆H₄-CH=CCl₂ | CH₃-C₆H₄-CH₂COOH | 94.8 | m.p. 94–95° C. |
| 38 | CH₂=CHCH₂O-, Cl-C₆H₃-CH=CCl₂ | CH₂=CHCH₂O-, Cl-C₆H₃-CH₂COOH | 92.8 | m.p. 92–93° C. |

I claim:

1. A process for preparing an aryl acetic acid derivative represented by the formula Ar(CH₂COY)$_n$ wherein Ar is phenyl, polynuclear aromatic group or heterocyclic group optionally substituted with halogen, hydroxyl, alkyl, alkenyl, aralkyl, alkoxy, acyloxy, aralkyloxy or phenoxy having or having not substituents, the substituent of said Ar is 1 to 3 in number and may be different or the same, n is an integer of 1 to 3, and Y is hydroxyl, or alkoxy, the process comprising hydrolyzing a dichloroethenyl compound represented by the formula Ar(CH=CCl₂)$_n$ when Ar and n are defined as above in the presence of about 0.01 to about 10 mole alkaline substance per mole of the dichloroethenyl compound in water and an organic solvent selected from the group consisting of methanol, ethanol and like alcohols, dimethylformamide, dimethylsulfoxide, dioxane, tetrahydrofuran and like ethers, benzene, toluene and like aromatic hydrocarbons or a mixture thereof, said alkaline substance being selected from the group consisting of alkali metal hydroxides, alkaline earth metal hydroxides and alkali metal alkoxides.

2. A process as defined in claim 1 wherein the alkaline substance is selected from the group consisting of sodium hydroxide, potassium hydroxide and like hydroxides of alkali metals, calcium hydroxide, barium hydroxide and like hydroxides of alkaline earth metals, sodium methylate, potassium butoxide and like metal alkoxides, etc.

3. A process as defined in claim 1 wherein the reaction mixture is heated to 70° to 150° C.

* * * * *